United States Patent [19]

Giraudi et al.

[11] 3,960,899

[45] June 1, 1976

[54] PROCESS FOR THE PREPARATION OF 8,14-CEDRANOXIDE

[75] Inventors: Edouard Giraudi, La-Roquette-sur-Siagne; Paul José Teisseire, Grasse, both of France

[73] Assignee: Societe Anonyme des Etablissements, Roure-Bertrand-Fils & Justin Dupont, Paris, France

[22] Filed: Aug. 22, 1972

[21] Appl. No.: 282,764

[30] Foreign Application Priority Data

Sept. 3, 1971 France............................ 71.31875

[52] U.S. Cl..................... 260/346.2 M; 204/158 R; 260/343; 260/563 P; 260/631.5
[51] Int. Cl.$^2$........................................ C07D 307/00
[58] Field of Search ............................ 260/346.2 M

[56] References Cited
UNITED STATES PATENTS 3,522,276   7/1970   Gibson ........................ 260/346.2 M

OTHER PUBLICATIONS

Baggaley et al., Tetrahedron (1968) vol. 24, pp. 3399–3405.
Fieser et al., Reagents for Organic Synthesis, New York, John Wiley (1966) pp. 261, 262, 301–302, and 586.
Barton et al., J. Am. Chem. Soc. (1960) vol. 82, pp. 2640–2641.

*Primary Examiner*—John D. Randolph
*Assistant Examiner*—B. Dentz
*Attorney, Agent, or Firm*—Wallenstein, Spangenberg, Hattis & Strampel

[57] ABSTRACT

Processes for the preparation of 8,14-cedranoxide are disclosed, according to which 8,14-cedrane diol is prepared by reducing 8,14-cedranolide by treatment with the aid of diisobutyl-aluminum hydride followed by acid hydrolysis, or 8,14-cedrane diol is cyclized with dimethyl sulfoxide.

10 Claims, No Drawings

PROCESS FOR THE PREPARATION OF 8,14-CEDRANOXIDE

This invention is concerned with a process for the preparation of tetracyclic sesquiterpenes of the cedrene group and, in particular, with a process for the preparation of 8,14-cedranoxide.

According to the present invention there is provided a process for the preparation of 8,14-cedranoxide which comprises: (a) reducing 8,14-cedranolide with a hydride source and boron trifluoride in an ethereal solvent or (b) cyclising 8,14-cedranediol with dimethyl sulfoxide.

Hydride sources which may be used in the process variant (a) include lithium aluminumhydride and sodium aluminum hydride.

The ethereal solvents which may be used in the process variant (a) include diisopropyl ether, tetrahydrofuran and diethylene glycol dimethyl ether.

The reaction of the process variant (a) may be effected at any convenient temperature. When tetrahydrofuran is used as the solvent, the reaction may conveniently be effected at the reflux temperature of the reaction medium.

The process variant (a) proceeds smoothly and with high yields. Thus, for example, using lithium aluminumhydride and boron trifluoride etherate in refluxing tetrahydrofuran a yield of 66% may be obtained.

The reaction of process variant (b) is conveniently effected by dissolving 8,14-cedranediol in dimethyl sulfoxide and refluxing.

Both starting materials may be prepared from cedrol according to the following reaction scheme, which also shows the final conversion into 8,14-cedrane oxide.

Reaction Scheme

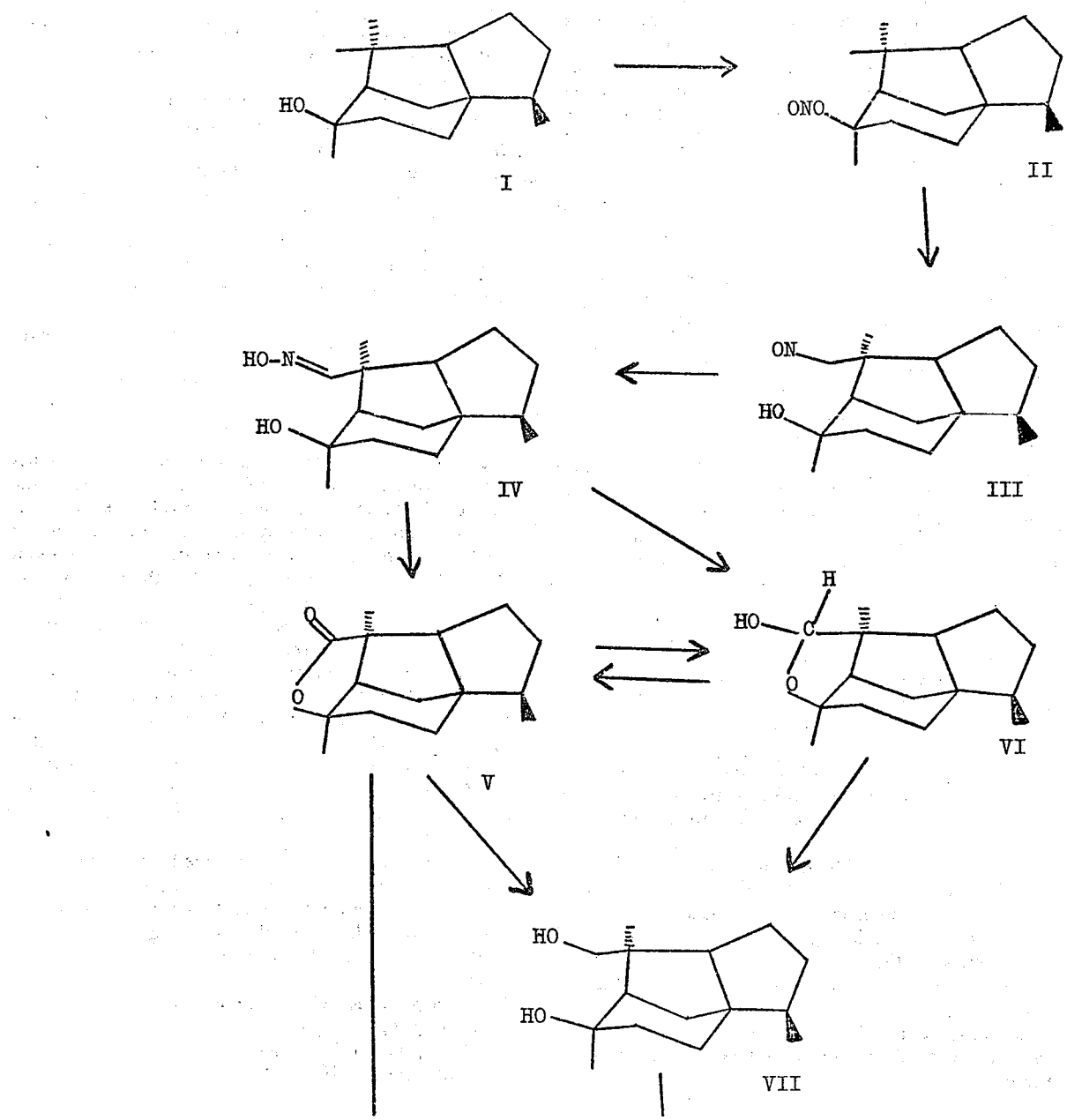

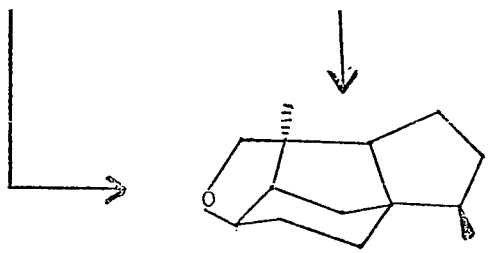

VIII 8,14-Cedranediol (VII) can be prepared from 8,14-cedranolide (V) or from the internal hemiacetal (VI). The internal hemiacetal (VI) can be prepared either from 8,14-cedranolide or from the 14-oximino-8-hydroxyl compound (IV). As a further variation the internal hemiacetal (VI) may be converted into 8,14-cedranolide (V). However, the conversion of the 14-oximino-8-hydroxyl compound (IV) into 8,14-cedranolide is usually effected by hydrolysis and oxidation without isolating the hemiacetal formed as intermediate. It will thus be noticed that there exist various ways by which 8,14-cedranoxide can be obtained from the key intermediate 14-oximino-8-hydroxyl compound (IV), or from the internal hemiacetal (VI) which is another key intermediate.

In more detail the various conversions discussed in the preceding paragraph may be effected as follows:

8,14-Cedranolide can be converted into 8,14-cedranediol by reduction, for example with the aid of diisobutyl-aluminumhydride as reducing agent, followed by acid hydrolysis. The acid hydrolysis may be effected, for example, with the aid or dilute sulphuric acid or dilute hydrochloride acid. This reduction also leads to the formation of a certain quantity of the internal hemiacetal of formula (VI). Other reducing agents may also be used such as lithium aluminumhydride.

8,14-Cedranolide may be prepared by direct oxidation of the 14-oximino-8-hydroxyl compound of formula (IV), by means of chromic oxidation followed by hydrolysis. In this case, the reagent is conveniently an aqueous solution of chromic acid and sulfuric acid, which is added to a solution of the alcohol in acetone. This oxidation proceeds via the internal hemiacetal (VI).

Acid hydrolysis of the 14-oximino-8-hydroxyl compound (IV) gives the internal hemiacetal (VI). The hemiacetal may be reduced to the glycol, 8,14-cedrandiol (VII), for example by treatment with lithium aluminumhydride.

The preparation of the 14-oximino-8-hydroxyl compound (IV), from cedrol is effected by treating cedrol (I) with nitrous acid, followed by photolysis and heating. The reaction proceeds via the intermediate compounds (II) and (III). The nitrous acid may be formed in situ using an alkali metal nitrite, such as sodium nitrite, and a strong acid, such as sulfuric acid. For the photolysis an ultraviolet light source is used. The final heating step to the formation of the 14-oximino-8-hydroxyl compound is conveniently effected on a water-bath.

The compounds 8,14-cedranolide and 8,14-cedrane oxide are both valuable in perfumery, having a woody-amber aroma.

The invention will now be illustrated with reference to the following Examples.

EXAMPLE 1

50 g of sodium nitrite, dissolved in 190 ml of water, were added to a solution of 111 g of cedrol (I) in 1,600 ml of petroleum ether, then 18 ml of concentrated sulphuric acid, diluted with 14 ml of water, were added with stirring over 1 hour and 30 minutes, keeping the temperature at 0° + 2°C.

As soon as the addition was finished the mixture was washed with 100 ml of a 10% aqueous solution of sodium carbonate and with water until neutral. The product was then dried over sodium sulphate and the latter was filtered off; the solution was then made up to 2000 ml with petroleum ether.

Thin-layer chromatography (elution, 15% ethyl acetate/petroleum ether, development, 50% $H_2SO_4$) allowed the detection of the presence of a little residual cedrol.

The cedryl nitrite (II) obtained had the following characteristics:

IR: $\nu$ 1620, 1375–1385, 800, 700–750 cm$^{-1}$.

EXAMPLE 2

The solution of cedryl nitrite obtained in accordance with Example 1 was photolyzed in a 2.5 liter four-necked Pyrex apparatus. In the central neck there was placed a double-walled cylindrical Pyrex receptacle, cooled in its external part by circulation of water and in the interior of which was placed a Philips UV high pressure HPK 125 lamp. A side neck was furnished with a heater the other two being the nitrogen inlet and outlet. Stirring was effected magnetically.

The photolysis was effected keeping the temperature at 10°C. The reaction was followed using T.L.C. (elution, 15% ethyl acetate/petroleum ether, developing agent, 50% $H_2SO_4$). The reaction was complete after 32 hours of irradiation. On completion of the reaction T.L.C. shows cedrol already present in the starting material and one or more polar products which are not eluted.

The petroleum ether was distilled on a water-bath, finishing under reduced pressure. There were thus obtained 122.4 g of crude product containing 14-nitrosocedrane-8-ol (III) having the following characteristics:

IR: $\nu$3340, 1,125, 1,200cm$^{-1}$

NMR:
    0,85 ppm methyl doublet J= 7 Hz
    1.02 ppm methyl singlet
    1.28 ppm methyl singlet
    4.86 ppm —CH$_2$— AB system J = 14 Hz.

The product was a mixture of two forms which gave a single form after 24 hours.

EXAMPLE 3

The crude reaction product obtained according to Example 2, was heated for 30 hours on a water-bath. 14-Oximino-cedrane-8-ol (IV) resulted. The product was used without working up in the next stage.

EXAMPLE 4

The product obtained in accordance with Example 3, was dissolved in 2000 ml of acetone. To this solution was added with stirring over 2 hours at a temperature of 20° ± 5°C, 410 ml of a solution 127 g of chromic oxide dissolved in 107 ml of concentrated sulphuric acid and 360 ml of water. Stirring was continued for 2 hours after the addition. The mixture was then cooled to 0°C and hydrolysed with 500 ml of methanol and then 1000 ml of water. 1,000 ml of methylene chloride were added. The aqueous phase was separated and extracted with 3 × 500 ml of methylene chloride. The combined organic phases were washed with 500 ml of 9% aqueous sodium bicarbonate, then with water until neutral. The mixture was dried over sodium sulphate and the solvent distilled on the water-bath, finishing under reduced pressure. 110 g of product were obtained.

Rectification in a Vigreux flask under a pressure of 0.3 mm Hg gave firstly, 23 g of unreacted crystallized cedrol followed by 55 g of 8,14-cedranolide (V) having a boiling point b.p.$_{0.3}$ = 137°C.

Yield based on amount of cedrol used: 59%.

The product had the following characteristics:
IR: $\nu$ 1760, 1235cm$^{-1}$
NMR:
0,89 ppm — CH$_3$ doublet J = 7 Hz
1.17 ppm — CH$_3$ singlet
1.34 ppm — CH$_3$ singlet

EXAMPLE 5

A solution of 11.7 g of 8,14-cedranolide (V) (0.05 mole) and 142 g of boron trifluoride etherate (1 mole) in 200 ml of anhydrous tetrahydrofuran was added with stirring over 1 hour and 15 minutes at reflux to a suspension of 4.2 of lithium aluminum hydride (0.11 mole) in 200 ml of anhydrous tetrahydrofuran.

The stirring and the heating at reflux were continued for 1 hour after the end of the addition. The mixture was then cooled to 0°C and hydrolyzed with 100 ml of a 10% aqueous solution of hydrochloric acid. 150 ml of petroleum ether were added and the aqueous phase was prepared. The aqueous phase was then extracted with 3 × 100 ml of petroleum ether. The combined organic phases were washed with 2 × 100 ml of a 9% aqueous solution of sodium bicarbonate and then with water until neutral.

Rectification in a Vigreux flask yielded 7.7 g of 8,14-cedranoxide (VIII) (purity 99% according to gas chromatography). Yield = 66%.

b.p.$_{0.45}$ = 86°C
IR: $\nu$ C-O tetrahydrofuran at 1,045 cm$^{-1}$
NMR:
0.82 ppm — CH$_3$ doublet J = 7 Hz
0.97 ppm — CH$_3$ singlet
1.08 ppm — CH$_3$ singlet
3.39 ppm — CH$_2$—O— AB system, J~8 Hz

EXAMPLE 6

55.8 ml of diisobutyl-aluminum hydride in 72.4 ml of petroleum ether were added with stirring and under nitrogen, over 1 hour and 30 minutes, to a solution of 27 g of 8,14-cedranolide (V) in 59.4 ml of petroleum ether. The temperature was allowed to rise from 21° to 35°C in the course of the addition. The mixture was then refluxed for 3 hours. The reaction medium was then cooled and hydrolyzed with 26 ml of ethanol, then 420 ml of a 10% aqueous solution of sulphuric acid. The product was taken up with 100 ml of methylene chloride, the organic phase isolated and the aqueous phase again extracted with 3 × 100 ml of methylene chloride. The combined organic phases were washed with 100 ml of a 10% aqueous solution of sodium bicarbonate and then with water until neutral. The resulting mixture was dried over sodium sulfate and the solvent distilled on the water-bath, finishing under a pressure of 20 mm Hg. 32.5 g of crystallized crude product were obtained.

8,14-Cedranediol can be isolated in the pure state using chromatography on a silica gel column. At the same time minor proportions of the 8,14-hemiacetal of cedrol of formula (VI) was formed as a by-product.

The physical characteristics of the 8,14-cedranediol obtained were as follows:
IR:
$\nu$ 3250, 1025, 1115cm$^{-1}$
free OH study:
3615 cm$^{-1}$ tertiary OH
3631 cm$^{-1}$ (shoulder) primary OH
3526 cm$^{-1}$ strong band OH . . . O
M.P. = 147°C
NMR:
0.83 ppm — CH$_3$ doublet J = 7 Hz
1.09 ppm — CH$_3$ singlet
1.29 ppm — CH$_3$ singlet
centered at 3.7 ppm —CH$_2$—(OH) AB system J 11 Hz
Mass: M = 238

The physical characteristics of the internal hemiacetal of formula (VI) obtained were as follows:
$\nu$ 3400, 1080, 1030, 1005 cm$^{-1}$
0.83 ppm — CH$_3$ doublet
1.00 ppm — CH$_3$ singlet
1.30 ppm — CH$_3$ singlet
4.36 ppm — H singlet
4.90 ppm — H singlet.

EXAMPLE 7

A solution of 32.5 g of 8,14-cedranediol in 230 ml of dimethyl sulfoxide was refluxed for 80 hours. The conversion of 8,14-cedranediol into 8,14-cedraneoxide was complete according to thin layer chromatography (elution, 25% ethyl acetate/petroleum ether, developing agent, 50% H$_2$SO$_4$).

The mixture was taken up with 500 ml of water and 500 ml of petroleum ether, filtered over sintered glass and the two phases were separated. The aqueous phase was extracted with 2 × 250 ml of petroleum ether. The combined organic phases were washed with 3 × 200 ml of water. They were then dried over sodium sulphate and the solvent was distilled, finishing under reduced pressure. 26 g of crude product were obtained.

Distillation in a Vigreux flask yielded 10.6 g of 8,14-cedraneoxide (purity 95% according to gas chromatography).

b.p.$_{0.1}$ = 76°–78°C.
Yield based an 8,14-cedranolide employed: 40%.

We claim:
1. A process for preparing 8,14-cedranoxide starting from cedrol, which comprises the following steps, taken in sequence:
   a. treating cedrol with nitrous acid to form cedryl nitrite,
   b. subjecting cedryl nitrite prepared according to step (a) to photolysis to form 14-nitroso-cedran-8-ol,
   c. heating the 14-nitroso-cedran-8-ol prepared according to step (b) to form 14-oximino-cedran-8-ol,
   d. converting 14-oximino-cedran-8-ol prepared according to step (c) to 8,14-cedrandiol, and
   e. cyclizing said 8,14-cedranediol with dimethyl sulfoxide to form 8,14-cedranoxide.

2. A process as claimed in claim 1, wherein the 8,14-cedranediol is prepared by reducing 8,14-cedranolide by treatment with the aid of diisobutyl-aluminum hydride followed by acid hydrolysis.

3. A process as claimed in claim 2, wherein the 8,14-cedranolide is prepared by oxidation of the oximino-alcohol of formula:

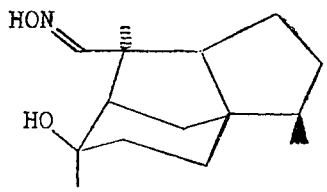

IV

4. A process as claimed in claim 2, wherein the 8,14-cedranolide is prepared from the oximino-alcohol of formula (IV) by hydrolysis followed by a chromic oxidation.

5. A process as claimed in claim 1, wherein the cyclizing is effected under refluxing with the 8,14-cedranediol being in solution in the dimethyl sulfoxide.

6. The process of claim 1, in which the conversion of 14-oximino-cedran-8-ol to 8,14-cedrandiol is effected by acid hydrolysis to form the internal hemiacetal of the formula

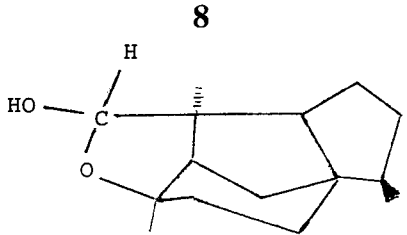

VI followed by reduction.

7. The process of claim 6, wherein the reduction is effected with lithium aluminum hydride.

8. The process of claim 1, in which the conversion of 14-oximino-cedran-8-ol to 8,14-cedrandiol is effected by acid hydrolysis to form the internal hemiacetal of the formula

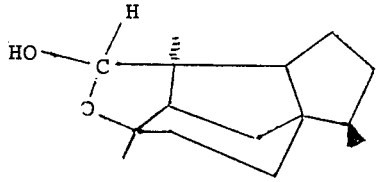

VI and by oxidation of said hemiacetal to form 8,14-cedranolide and conversion of said 8,14-cedranolide to 8,14-cedrandiol.

9. The process of claim 1, in which step (d) is effected by chromic oxidation of the 14-oximino-cedran-8-ol followed by acid hydrolysis to form 8,14-cedranolide, followed by reduction of said 8,14-cedranolide and acid hydrolysis.

10. The process of claim 9, in which the reduction is effected with diisobutyl aluminum hydride.

* * * * *